(12) United States Patent
Kane et al.

(10) Patent No.: US 11,869,182 B2
(45) Date of Patent: Jan. 9, 2024

(54) SYSTEMS AND METHODS FOR SEGMENTATION AND MEASUREMENT OF A SKIN ABNORMALITY

(71) Applicant: Fuel 3D Technologies Limited, Oxford (GB)

(72) Inventors: Chris Kane, Oxford (GB); Leonardo Rubio Navarro, Oxford (GB); Adeala Zabair, Oxford (GB); Anna Chabokdast, Oxford (GB); James Klatzow, Oxford (GB)

(73) Assignee: Fuel 3D Technologies Limited, Oxford (GB)

( * ) Notice: Subject to any disclaimer, the term of this patent is extended or adjusted under 35 U.S.C. 154(b) by 477 days.

(21) Appl. No.: 17/252,217

(22) PCT Filed: Jun. 14, 2019

(86) PCT No.: PCT/GB2019/051657
§ 371 (c)(1),
(2) Date: Dec. 14, 2020

(87) PCT Pub. No.: WO2019/239147
PCT Pub. Date: Dec. 19, 2019

(65) Prior Publication Data
US 2021/0366108 A1     Nov. 25, 2021

(30) Foreign Application Priority Data

Jun. 14, 2018  (GB) ...................................... 1809768
Nov. 8, 2018  (GB) ...................................... 1818241

(51) Int. Cl.
*G06T 7/00*  (2017.01)
*G06T 7/11*  (2017.01)
(Continued)

(52) U.S. Cl.
CPC ............ *G06T 7/0012* (2013.01); *A61B 5/004* (2013.01); *A61B 5/444* (2013.01); *A61B 5/7264* (2013.01);
(Continued)

(58) Field of Classification Search
CPC . G06T 7/0012; G06T 3/40; G06T 7/11; G06T 7/12; G06T 7/187; G06T 7/40;
(Continued)

(56) References Cited

U.S. PATENT DOCUMENTS

2013/0018271 A1   1/2013   Mohamad Hani et al.
2013/0162796 A1   6/2013   Bharara et al.
(Continued)

FOREIGN PATENT DOCUMENTS

EP        0885587 A1      12/1998
WO    WO-2018122793 A1 *  7/2018    ............. G06T 15/04

OTHER PUBLICATIONS

Search Report, UK Patent Application No. GB1818241.0, dated May 7, 2019 (3 pages).
(Continued)

*Primary Examiner* — Jon Chang
(74) *Attorney, Agent, or Firm* — Thomas Horstemeyer, LLP

(57) ABSTRACT

A method is proposed for identifying ("segmenting") at least one portion of the skin of an animal which is a region of interest (e.g. a portion which is subject to an abnormality such as a tumor). The method uses at least a temperature dataset obtained by measuring the temperature of each of a plurality of points of a region of the skin. An initial segmentation may be performed using the temperature data based on a statistical model, in which each point is segmented based on its temperature and optionally that of its neighbors. The initial segmentation based on the tempera-
(Continued)

ture data may be improved using a three-dimensional model of the profile of the skin, and the enhanced segmentation may be used to improve the three-dimensional model.

14 Claims, 8 Drawing Sheets

(51) Int. Cl.
| | |
|---|---|
| *G06T 7/12* | (2017.01) |
| *G06T 7/174* | (2017.01) |
| *G06T 7/187* | (2017.01) |
| *G06T 7/64* | (2017.01) |
| *G06T 7/62* | (2017.01) |
| *G06T 7/50* | (2017.01) |
| *A61B 5/00* | (2006.01) |
| *G06T 3/40* | (2006.01) |
| *G06T 7/40* | (2017.01) |
| *G06T 19/20* | (2011.01) |
| *G06F 18/2431* | (2023.01) |

(52) U.S. Cl.
CPC ............ *G06F 18/2431* (2023.01); *G06T 3/40* (2013.01); *G06T 7/11* (2017.01); *G06T 7/12* (2017.01); *G06T 7/187* (2017.01); *G06T 7/40* (2013.01); *G06T 7/50* (2017.01); *G06T 7/62* (2017.01); *G06T 7/64* (2017.01); *G06T 19/20* (2013.01); *A61B 2503/40* (2013.01); *G06T 7/174* (2017.01); *G06T 2207/10048* (2013.01); *G06T 2207/20084* (2013.01); *G06T 2207/30088* (2013.01); *G06T 2207/30096* (2013.01); *G06T 2219/2021* (2013.01); *G06V 2201/03* (2022.01); *G06V 2201/032* (2022.01)

(58) Field of Classification Search
CPC .... G06T 7/50; G06T 7/62; G06T 7/64; G06T 19/20; G06T 2207/10048; G06T 2207/20084; G06T 2207/30088; G06T 2207/30096; G06T 2219/2021; G06T 2207/10028; G06T 7/174; G06V 2201/03; G06V 2201/032; A61B 5/004; A61B 5/444; A61B 5/7264; A61B 2503/40; G06F 18/2431

See application file for complete search history.

(56) References Cited

U.S. PATENT DOCUMENTS

| | | |
|---|---|---|
| 2017/0193659 A1 | 7/2017 | Wang et al. |
| 2018/0122071 A1 | 5/2018 | Bozorgtabar et al. |
| 2021/0124977 A1* | 4/2021 | Panetta ................. G06V 10/40 |

OTHER PUBLICATIONS

Search Report and Written Opinion, International Patent Application PCT/GB2019/051657, dated Sep. 20, 2019 (12 pages).
Grubisic, Ivan et al., "Active 3D scanning based 3D thermography system and medical applications," MIPRO, 2011 Proceedings of the 34th International Convention, IEEE, May 23, 2011, pp. 269-273.
Song, Chengli et al., "Thermographic Assessment of Tumour Growth in Mouse Xenografts," International Journal of Cancer (2007), vol. 121, Issue 5, pp. 1055-1058.
Smith, Andrew, "Are Calipers Obsolete? 3D Subcutaneous Tumor Scanning and the Lab of the Future," Jan. 26, 2018, retrieved from the internet on Aug. 5, 2019, https://www.laboratoryequipment.com/article/2018/02/are-calipersobselete.
Dehmeshki, Jamshid, "An adaptive segmentation and 3-D visualisation of the lungs," Pattern Recognition Letters 20 (1999) Elsevier, pp. 919-926.
Bazi, Yakoub, et al., "Image thresholding based on the EM algorithm and the generalized Gaussian distribution," ScienceDirect, Pattern Recognition 40 (2007), pp. 619-634.
San Martin, Ja Delgado, et al., "Non-invasive 3D time-of-flight imaging technique for tumour volume assessment In subcutaneous models," Laboratory Animals, vol. 49(2), (2015), pp. 168-171.
Luca, M. Di, et al., "Inconsistency of perceived 3D shape," Vision Research 50, (2010), pp. 1519-1531.
Wilson, Zena, et al., "A 3D scanning tehcnology to measure subcutaneous tumour volume. Are callipers obsolete?," AstraZenca (2 pages), 2018.
Combined Search and Examination Report, Patent Application GB1809768.3, dated Dec. 14, 2018 (7 pages).

* cited by examiner

SYSTEMS AND METHODS FOR SEGMENTATION AND MEASUREMENT OF A SKIN ABNORMALITY

CROSS-REFERENCE TO RELATED APPLICATION

This application is the 35 U.S.C. § 371 national stage application of PCT Application No. PCT/GB2019/051657, filed Jun. 14, 2019, where the PCT claims priority to and the benefit of, GB Patent Application No. 1809768.3, filed Jun. 14, 2018, and GB Patent Application No. 1818241.0, filed Nov. 8, 2018, all of which are herein incorporated by reference in their entireties.

FIELD OF THE INVENTION

The present invention relates to an imaging method and an imaging system for generating three-dimensional (3D) images of a region of interest on skin, e.g. a region of interest associated with a three-dimensional abnormality such as a tumor or wound on the body of an animal, especially a mammal, such as a rat or other rodent. It further relates to a method and system for extracting numerical data characterizing the abnormality.

BACKGROUND OF THE INVENTION

Much laboratory research involves studying growths and/or wounds on the skin of a laboratory animal such as a rat or other mammal. In particular, subcutaneous growths such as tumors are often studied. For example, in the case of a laboratory animal which is subject to a treatment regime, measurements of the extent and/or the growth speed of tumors give useful information about the treatment regime. The tumors may be measured laterally (that is, their extent parallel to the skin surface) or by their protrusion (that is, their extent perpendicular to the skin surface). Other research involves measurement at intervals of wounds on the skin of a laboratory animal, i.e. cavities in the skin, e.g. to measure how quickly wounds heal (or expand).

Conventionally, measurements of growths/cavities are obtained manually using calipers, often after the animal has been shaved. This has several disadvantages: it is subject to human error; and it is somewhat subjective since different laboratory workers may measure tumors in slightly different ways (e.g. measuring different positions on the tumor), and may apply different levels of compression to the tumor using the calipers. The measurement process may be time-consuming and have insufficient repeatability.

Recently methods have been proposed for automatically obtaining a three-dimensional model of the animal's skin. The profile of the skin (that is, the three-dimensional shape of the surface of the skin) is obtained by methods such as laser scanning, photometry or stereoscopy. However, it is technically challenging to process the resulting dataset, because it is hard to determine how much of the shape of the model is due to the abnormality and how much is due to the natural curvature of the skin of the animal.

SUMMARY OF THE INVENTION

In general terms, the present invention proposes identifying at least one portion of the skin of an animal which is a region of interest (e.g. an abnormality) using at least a temperature dataset obtained by measuring the temperature of each of a plurality of points of a region of the skin. The identification process may be referred to as "segmentation", i.e. segmenting (classifying) the skin into the at least one portion of the skin which is part of a region of interest, and other portion(s) of the skin which are not part of the region of interest. This concept is based on the observation that certain skin abnormalities change the distribution of temperatures on the skin. For example, for many tumors the temperature of the skin above the tumor is lower than that of surrounding skin.

The region of interest may be any portion of the skin which is expected to be at a different temperature from a neighboring portion of the skin. For example, it may be a portion having a high or low proportion of hair compared to the neighboring portion of the skin. However, more typically, it is a portion which is subject to an abnormality which changes the temperature of the skin, e.g. a tumor, or possibly a wound.

The temperature dataset is preferably used in combination with a model of the three-dimensional profile of the skin. In this respect the temperature dataset is "fused" with the three-dimensional model of the profile of the skin, e.g. to obtain an enhanced segmentation of the skin and/or an improved three-dimensional model. The model of the skin may, for example, be obtained by combining images of the region of the skin captured using a plurality of cameras. For example, the images may be combined using stereoscopy to create the model.

In one example, an initial segmentation may be obtained based on the temperature dataset (for example as explained below), and may be enhanced using the three dimensional model of the profile of the skin. For example, if the initial segmentation identifies a certain portion of the skin as being part of the region of interest, but a corresponding portion of the model of the three-dimensional profile of the skin does not meet a criterion indicative of the region of interest (for example, if the portion of the model obeys a continuity criterion with respect to another neighboring or surrounding portion of the skin), the portion of the skin may be re-classified as not being part of the region of interest.

In another example, which can be combined with the first, a segmentation obtained using the temperature data, is used to improve at least a part of the three-dimensional model of the profile of the skin. For example, the improvement may improve a defective portion of the three-dimensional model, such as a portion which is missing, or which is determined to meet a criterion indicative of being low accuracy. Specifically, the improvement may add an interpolation surface to at least part of the defective portion of the three-dimensional model of the profile of the skin. The interpolation surface may have a first edge which, according to the segmentation based on the temperature data (e.g. the enhanced segmentation), is at edge of the portion of the skin which is part of the region of interest. At a second edge of the interpolation surface, which according to the segmentation is in a portion of the skin which is part of the region of interest, the interpolation surface may be continuous with, and optionally may have a gradient equal to that of, the three-dimensional model at the other side of the second edge.

One or more numerical parameters characterizing the region of interest may then be derived (e.g. automatically) from the modified three-dimensional model of the profile of the skin, e.g. a value indicative of the volume of an abnormality associated with the region of interest. For example, the numerical parameter(s) may comprise a volume between the modified three-dimensional model and a baseline surface, which is an estimate of what the surface of the skin would have been in the absence of the abnormality.

As mentioned above, an initial segmentation of the portion of the skin which is part of the region of interest may be formed using the temperature data. Specifically, the initial segmentation of the skin based on the temperature dataset may be based on whether each point of the region of the skin has a temperature, according to the temperature dataset which is above or below a cut-off temperature. Note that as explained below, the cut-off temperature may be the same for all skin points, or may be different for different respective points of the skin. The cut-off temperature(s) are derived from the temperature dataset.

For example, the cut-off temperature(s) may be derived from a statistical model of statistical variation of temperature within a region of the skin containing both skin which is part of the region of interest and skin which is not part of the region of interest. The cut-off temperature for a given point of the skin may be a temperature at which the point of the skin is equally likely according to the statistical model to be part or not part of the region of interest.

The statistical model may be characterized by a first temperature value indicative of an average (e.g. mean) temperature of skin points which are part of the region of interest, and a second temperature value indicative of an average (e.g. mean) temperature of skin points which are not part of the region of interest. The statistical model may be further characterized by a first variance value indicative of a temperature variability of skin points which are part of the region of interest, and a second variance value indicative of a temperature variability of skin points which are not part of the region of interest. In other words, according to the statistical model, the likelihood that any given point of the skin is part of the region of interest is also a function of the first and second temperature values, and optionally also the first and second variance values.

Furthermore, according to the statistical model, the likelihood that any given point of the skin is part of the region of interest may also be a function of the temperatures, according to the temperature data, of one or more other points on the skin which each meet a proximity criterion with respect to the given point. For example, the proximity criterion may be that the other point on the skin is within a certain distance of the given point. Thus, for any given skin point, the proximity criterion defines a neighborhood consisting of other skin points, and the cut-off temperature for the given skin point depends upon the temperature of the other skin points in the neighborhood.

For example, if the first temperature value is higher (or alternatively lower) than the second temperature value, according to the statistical model, the likelihood that a given skin point is part of the region of interest is an increasing (decreasing) function of the respective temperatures of the skin points in the corresponding neighborhood. In other words, according to the statistical model, the given skin point is more likely to be part of the region of interest if its neighboring pixels are warmer (colder).

The result of defining the statistical model in this way is that the effect of noise in the temperature dataset is reduced. This is because the temperature of a given point has to differ from the temperature of its neighboring points by a higher amount in order for the given pixel to be classified differently from its neighbors.

Optionally, an iterative procedure may be carried out in which, in each of a plurality of steps, an current estimate of one of more numerical parameters of the statistical model (e.g. the first and second temperature values, and/or the first and second variances) is used to perform a segmentation of the region of the skin, and the segmentation is used to produce an improved estimate of the numerical parameter(s).

The invention may be expressed in terms of a method or system for processing captured data relating to the region of the skin, for example to perform the segmentation, and/or to derive the numerical parameter(s) characterizing the abnormality. Alternatively, the invention may be expressed as a computer program product (e.g. stored in non-transitory form on a tangible recording medium) comprising program instructions operative when implemented by a processor, to perform the method. Alternatively, the invention may be expressed as an imaging method or system which captures the data relating to the region of the skin, and then processes it by the method.

BRIEF DESCRIPTION OF THE DRAWINGS

An embodiment of the invention will now be described for the sake of example only with reference to the following figures in which.

DETAILED DESCRIPTION OF THE EMBODIMENTS

Figure 1:
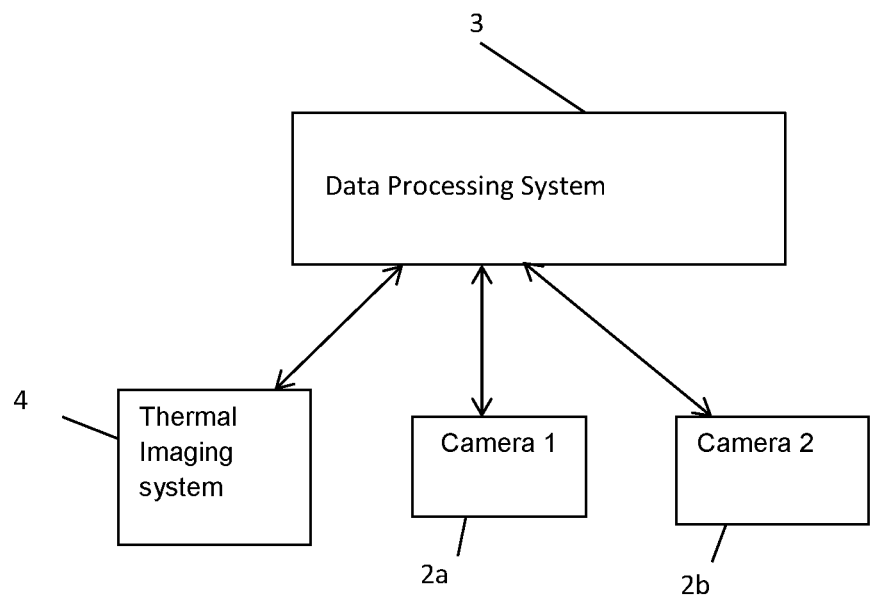
FIG. 1 is a schematic view of an imaging system which is an embodiment of the present invention.
Figure 1:
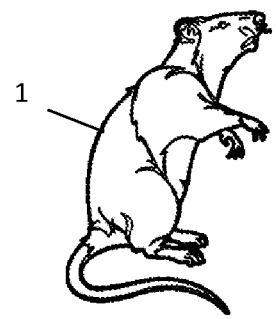

FIG. 1 shows schematically an imaging system which is an embodiment of the invention. The imaging system includes an imaging region where at least part of an animal 1 may be placed. The animal 1 may be hand-held or retained by a retention mechanism. The imaging region is in the field of view of one or more cameras 2*a*, 2*b*. The camera(s) produce respective two dimensional images of the field of view, from different respective imaging positions and optionally in different respective viewing directions. When an animal 1 is located in the field of view, each of the images captured by the cameras 2*a*, 2*b* comprises an image of a region of the skin of the animal 1. The animal 1 is typically positioned such that the region of skin contains the whole of a skin abnormality, such as a sub-cutaneous tumor or a wound.

Although the number of cameras is illustrated in FIG. 1 as two, there may be more or fewer cameras. Furthermore the cameras 2a, 2b may be operative to capture still images and/or video images, with both sorts of images being referred to as "images" in this document. The electromagnetic radiation captured by the camera(s) 2a, 2b may be in any frequency range, not necessarily the visible frequency range.

The outputs of the cameras 2a, 2b are transmitted to a data processing system 3. The construction of the data processing system 3 is explained below in more detail with reference to FIG. 8. The data processing system 3 is operative, using the images captured by the cameras 2a, 2b, to construct a three-dimensional numerical model of the region of the skin of the animal 1. In one possibility, the three-dimensional model may be constructed by stereoscopy. In a further possibility, the three-dimensional image may be constructed using photometry, for example using the photometric technique employed in WO 2009/122200, the disclosure of which is incorporated herein by reference. In a further possibility, photometry and stereoscopy may be combined. Furthermore, the cameras 2a, 2b may be replaced (or supplemented) with e.g. a laser imaging system, or ultrasound imaging system, which measures reflections of a beam moved (e.g. in a raster) to successive points of the skin region, and forms a depth image of the region of the skin from the measurement results.

The imaging system further comprises a thermal imaging system 4 (typically an infra-red camera) which is operative to capture a thermal image (temperature dataset) indicating the respective temperatures of a plurality of points of the region of the animal's skin. Thus, the temperature dataset comprises a two-dimensional thermal image of the region of the skin. The temperature dataset is transmitted to the data processing system 3.

Optionally, e.g. to reduce noise, any of the thermal imaging system 4 and/or the cameras 2a, 2b may capture multiple images at different respective times and combine them with each other (e.g. by averaging). Thus, for example, the temperature dataset referred to above may in fact be formed by averaging multiple thermal images captured by the thermal imaging system 4 at different respective times, optionally with a selected alignment of the images to compensate for movement of the animal 1 in the time periods between the times that the respective thermal images were captured.

The temperature dataset may for example be a respective temperature value for each of a two-dimensional array of points (pixels) which correspond under a first mapping to an array of respective points spanning the region of the skin of the animal. Thus, the first mapping (which depends on the position of the thermal imaging system relative to the region of the skin) maps the curved region of the skin to a (flat) two-dimensional space in which the thermal image is defined.

Similarly, each of the images captured by the camera(s) 2a, 2b is a set of intensity values (optionally for each of a plurality of colors) for each of a two-dimensional array of pixels. The pixels correspond, under a respective second mapping for each camera, to points of the region of the skin. Thus, a small sub-area of the typically curved region of the skin (e.g. what is referred to below as "a point of the skin") corresponds under the first mapping to a first number of points in the thermal image, and under each of the second mappings to a respective second number of points in the respective images captured by the camera(s) 2a, 2b. The ratios of the first number and the second numbers depend upon the resolutions of the cameras 2a, 2b and the thermal imaging system 4. In this document, the temperature of a "point of the skin" may refer to a mean of the temperatures of the points in the temperature dataset which correspond to the point of the skin under the first mapping. For simplicity, the following explanation refers to "segmenting the region of skin" (i.e. assigning portions of it to a corresponding one of multiple classes), and the segmentation referred to is to be understood as being performed in any one of these corresponding discrete two-dimensional spaces, or in yet another discrete two-dimensional space which corresponds by another mapping to the surface of the skin. For example, conveniently the segmentation may be performed in the two-dimensional space in which the temperature dataset is defined, or in a discrete two-dimensional space having a lower resolution than the thermal image and the images captured by the cameras 2a, 2b.

Although the thermal imaging system 4 is illustrated as being separate from the camera(s) 2a, 2b which capture the images used to construct the three-dimensional model of the profile of the region of the skin, in other embodiments the thermal image itself might be used to generate the three-dimensional model. For example, the imaging system might comprise a plurality of thermal imaging systems 4 producing respective thermal images from different respective imaging positions, and stereoscopy might be performed on the plurality of thermal images to produce the three-dimensional model of the profile of the skin.

Figure 2:
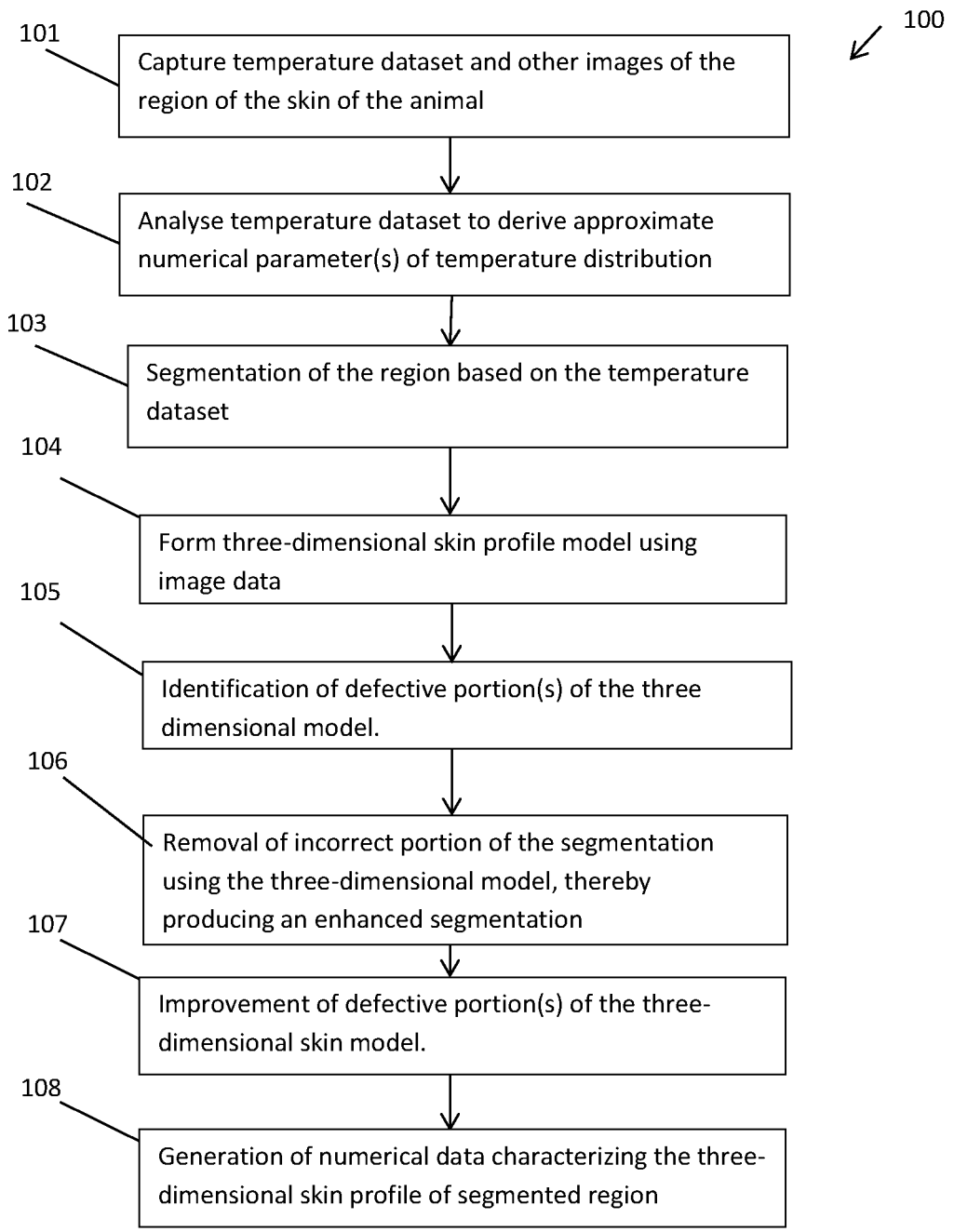
FIG. 2 is a flow diagram of a method which is an embodiment of the invention.

Turning to FIG. 2, a method 100 is illustrated which is performed by the imaging system of FIG. 1, and which is an embodiment of the method.

In step 101, the thermal imaging system 4 is used to capture the temperature dataset (a temperature map), and the camera(s) 2a, 2b are used to capture other images of the region of the skin of the animal. Thus, step 101 is carried out by the thermal imaging system 4 and the cameras 2a, 2b under the control of the data processing system 3.

The remaining steps of method 100 are performed by the data processing system 3 alone. In step 102 numerical parameter(s) of the temperature distribution are obtained from the temperature dataset. These may include a cut-off temperature used in step 103 to perform segmentation.

Figure 3:
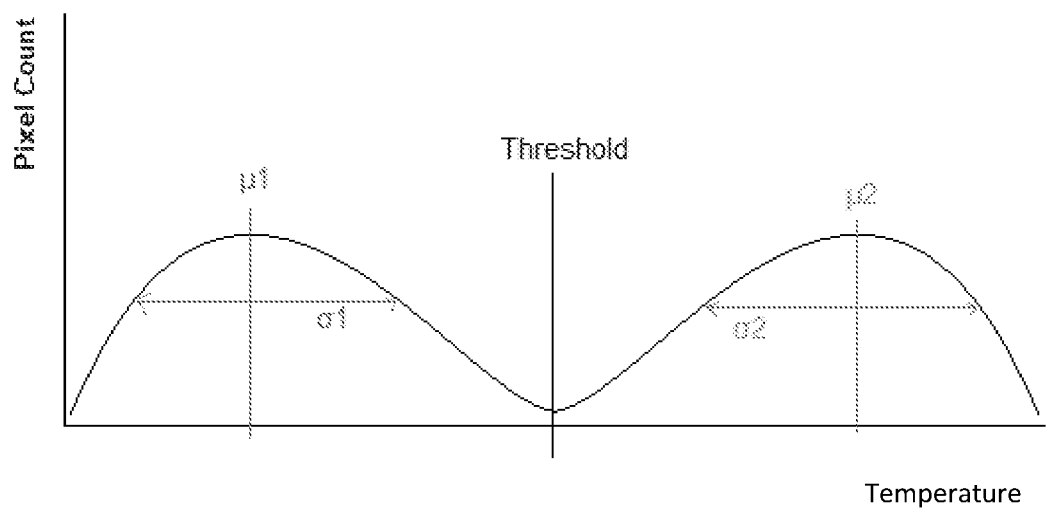
FIG. 3 illustrates a first possible statistical model used in the method of FIG. 2.

For example, in step 102, a histogram may be plotted of the number of the pixels of the temperature data against temperature (that is, the histogram indicates, for each of a sequence of non-overlapping temperature ranges, the respective number of points (pixels) of the skin region having a temperature in that range). The result would ideally be as shown in FIG. 3. That is, there are may be two peaks, with a dip between them. This is because it is expected that points which are subject to the abnormality (e.g. subject to a tumor, or any other abnormality which changes the temperature of the skin) would have a temperature which is distributed as a Gaussian distribution with a first mean temperature value (denoted $\mu_1$) and a first variance value (denoted $\sigma_1$), and that points which are not subject to the abnormality would have a temperature which is distributed as a Gaussian distribution with a second mean temperature value (denoted $\mu_2$) and a first variance value (denoted $\sigma_2$). The values of the first and second temperature values $\mu_1$ and $\mu_2$, and the first and second variance values $\sigma_1$ and $\sigma_2$ may not be known in advance (and indeed it may not be pre-known which of the first and second temperature values is higher, and/or which of the first and second variance values is higher). The histogram in FIG. 3 is thus likely to be approximately a sum of two Gaussian curves, each having an amplitude which depends of the proportion of the region of the skin which is subject to the abnormality. Note that due to noise in the temperature data the true first and second temperature values $\mu_1$ and $\mu_2$ will not correspond exactly to the maxima in the histogram of FIG. 3. Nevertheless, the value of $\mu_1$ and $\mu_2$ may be approximated as the two temperatures corresponding to the peaks of the histogram of FIG. 3. Similarly, the variance values variance values $\sigma_1$ and $\sigma_2$ may be approximated from the respective widths of the peaks.

In an ideal case, the cut-off temperature could be chosen based on a minimum point of the distribution, as shown in FIG. 3, between the peaks. However, in reality, the histogram is likely to contain noise, so that the distribution has multiple local minima between the peaks. One such minimum may be selected at random as the cut-off temperature, or the cut-off temperature may be set to be an average of the temperatures corresponding to the two peaks of the distribution (which may or may not themselves be well defined, depending upon the noise).

In step 103, using the temperature data and the numerical parameters (e.g. the cut-off value), the region of the skin is segmented. This may be done by determining points on the skin for which the temperature according to the temperature dataset is above or below the cut-off temperature.

Optionally, the cut-off temperature may be selected based on a statistical model of skin temperatures similar to that shown in FIG. 3, and based on numerical values (such as $\sigma_1$, $\sigma_2$, $\mu_1$ and $\mu_2$) which are estimated from the histogram of FIG. 3. For example, the cut-off temperature may be the temperature such that, according to the statistical model, the probability is 50% that a portion of the skin at that temperature is subject to the abnormality. Since the cut-off temperature depends upon the first and second temperature values $\mu_1$ and $\mu_2$, and the variance values $\sigma_1$ and $\sigma_2$, it can be said that each pixel of the skin region is segmented based on a statistical model which is a function of the temperature of the pixel according to the temperature dataset, and also the first and second temperature values $\mu_1$ and $\mu_2$, and the variance values $\sigma_1$ and $\sigma_2$. This can be referred to as an "expectation maximization" algorithm.

Figure 4A:
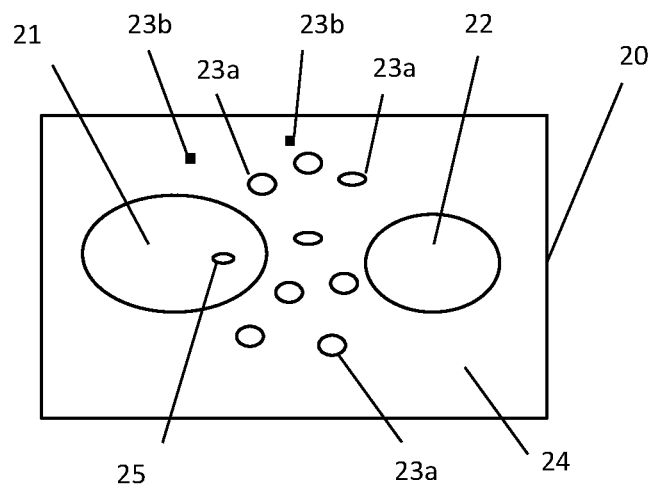
FIG. 4(*a*) shows a preliminary segmentation, produced in the method of FIG. 2, of a region of skin, to estimate a portion of the skin which is subject to an abnormality, and FIG. 4(*b*) shows an improved segmentation which may be produced from the preliminary segmentation.

The result of applying this cut-off temperature for the segmentation may be as shown in FIG. 4(a). Here the outer border of the region of the skin under consideration is indicated as 20. As shown in FIG. 4(a) a number of areas of the skin 21, 22, 23a, 23b have a temperature throughout which is above (or below) the cut-off temperature, while area 25, and also the area 24 which extends to the outer border 20 of the skin region 20, have a temperature which is below (or above) the cut-off temperature. The areas 23a, 25 are clusters of pixels, while the areas 23b are individual pixels. Depending upon whether the temperature of the region 24 is above or below the cut-off temperature, it can be determined which of the temperature values $\mu_1$ and $\mu_2$ is higher, if this is not pre-known. Note that, for a tumor, the first temperature value $\mu_1$ of the portion of the region of the skin which is subject to the tumor (i.e. overlies the tumor) may optionally be assumed to be lower than the second temperature value $\mu_2$ of the portion of the region of the skin which is not subject to the tumor. Note that in FIG. 4, the small areas 23a, 23b are likely to be the result of noise in the temperature dataset, e.g. due to blood vessels or hair on the surface of the animal, while one of the larger areas 21, 22 is likely to represent the tumor itself, at least approximately. The area 25 has a temperature on the other side of the cut-off temperature from the rest of the area 21, which surrounds it. Therefore, if the area 21 approximately represents the abnormality, the area 25 may well be a noise artifact (e.g. due to hair or a blood vessel on the tumor).

Optionally, in step 103 the segmentation may be performed using a more sophisticated statistical model, referred to here as a "modified expectation maximization" (MEM) model. MEMs were proposed in "An adaptive segmentation and 3-D visualization of the lungs" by J. Dehmeshki in Pattern Recognition Letters 20 (1999) 919-926, the disclosure of which is incorporated by reference, which dealt with the unrelated technical field of delineating lungs within computerized tomography images. According to this more sophisticated statistical model, the likelihood that any given point of the skin is subject to the abnormality may additionally be a function of the temperatures, according to the temperature dataset, of one or more other points on the skin which each meet a proximity criterion with respect to the given point. For example, the proximity criterion may be that the other point on the skin is within a certain distance of the given point. Thus, for any given skin point, the proximity criterion defines a neighborhood consisting of other skin points. The measure of distance may for example, be Euclidean distance in a two-dimensional space corresponding to the skin surface, or some other measure of distance, such as the Manhattan distance in the two-dimensional space.

To put this another way, each pixel of the skin region is segmented based on a statistical model in which the probability that it is (or is not) overlying the tumor is a function of (i) its own temperature, (ii) the first and second temperature values $\mu_1$ and $\mu_2$, and the first and second variance values $\sigma_1$ and $\sigma_2$, and (iii) the measured temperature of the neighboring pixels. The more sophisticated statistical model incorporates prior knowledge that points of the skin which are subject (or not subject) to the tumor have a high probability of containing other such points within their neighborhood. Thus, even if a given point has a temperature which is not associated with the abnormality, the point still has a high chance of being subject to the abnormality if it is neighbored by (e.g. is surrounded by) other points subject to the abnormality. The exact form for the statistical model (as given in Eqns. (5) and (6) of the above-referenced publication by J. Dehmeshki) is an a posteriori probability of the given point being in either of the two classes (i.e. subject to the abnormality or not) given the values $\sigma_1$, $\sigma_2$, $\mu_1$ and $\mu_2$, and the temperatures of the other points in its neighborhood. The cut-off temperature for the point on the skin is such that the a posteriori probability is 50% that the point is subject to the abnormality.

For example, considering the case that $\mu_1$ is lower than $\mu_2$, according to the statistical model the likelihood that a given skin point is subject to the abnormality may be a decreasing function of the respective temperatures of the skin points of the corresponding neighborhood. In other words, according to the statistical model, the given skin point is more likely to be subject to the abnormality if its neighboring pixels are colder.

The size of the neighborhood (i.e. the proximity criterion) may be chosen with prior knowledge of the abnormality. For example, if it is believed that the abnormality will be at least 10 pixels wide, the neighborhood may be chosen to have approximately this diameter. To express this more generally, the neighborhood is characterized by an extent (a distance parameter) which is based on prior knowledge of the associated normality.

Figure 4B:
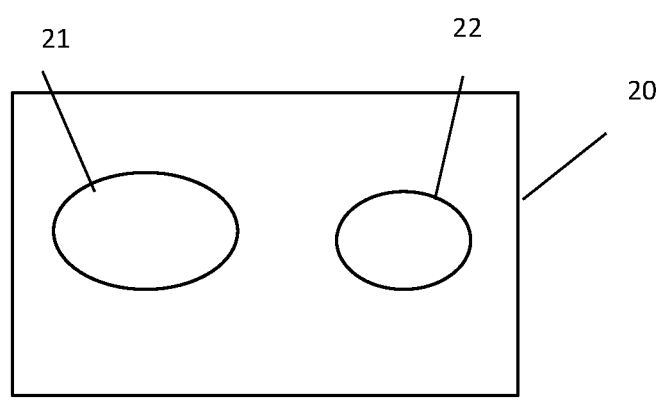

The result of defining the statistical model in this more sophisticated way is that noise in the thermal model is reduced. This is illustrated in FIG. 4(b) which shows schematically the result of using the MEM technique on the skin region 20. The effect of noise is reduced (i.e. areas 23a, 23b and 25 are eliminated) because the temperature of a given point in the temperature map (i.e. an individual pixel of the temperature map, or small cluster of pixels) has to differ from the temperature of its neighboring points by a higher amount in order for the given point to be classified differently from its neighbors.

Note that an alternative to performing the MEM using posterior probabilities is to downsample the temperature map (i.e. reduce its pixel resolution such that a single pixel of the downsampled map has a temperature which is an average of a respective neighborhood (a plurality of pixels) in the original temperature map), and comparing each pixel in the downsampled temperature map to the cut-off temperature. That is, the original temperature map may be downsampled to produce a downsampled map (e.g. using a multi-scale approach any number of times), and then each pixel of the downsampled temperature map is compared to the cut-off temperature. The segmentation is done based on the result of the comparison. Thus, the proximity criterion in this case is whether, following to the downsampling, two points of the original temperature map are mapped to the same pixel of the downsampled map by the downsampling operation. For example, if the original temperature map has a pixel resolution of 1024×1024, the depth map may be downsampled to 512×512, 256×256, 128×128, or 64×64. Compared to using the probabilisitic approach to MEM, the downsampling approach requires less computational effort. The prior knowledge of the abnormality can be used to select the amount of downsampling applied to the original temperature map.

Once this improved segmentation has been performed, the respective temperatures of the pixels corresponding to skin points which, according to the segmentation, are subject to the abnormality, may be used to produce improved values for the first temperature value $\mu_1$ and the first variance value $\sigma_1$. Similarly, the respective temperatures of the pixels corresponding to skin points which, according to the segmentation, are not subject to the abnormality, may be used to produce improved values for the second temperature value $\mu_2$ and the first variance value $\sigma_2$. The segmentation process using the more sophisticated statistical model (i.e. using the temperatures of neighboring pixels) can then be repeated using the improved values of $\sigma_1$, $\sigma_2$, $\mu_1$ and $\mu_2$.

Optionally, step 103 may include an iterative procedure in which, in each of a plurality of steps, (i) a current estimate of one of more numerical parameters of the statistical model (e.g. $\sigma_1$, $\sigma_2$, $\mu_1$ and $\mu_2$) is used to perform a segmentation of the region of the skin based on the more sophisticated statistical model employing respective neighborhoods for each pixel, and (ii) the segmentation is used to produce an improved estimate of the numerical parameter(s).

Figure 5:
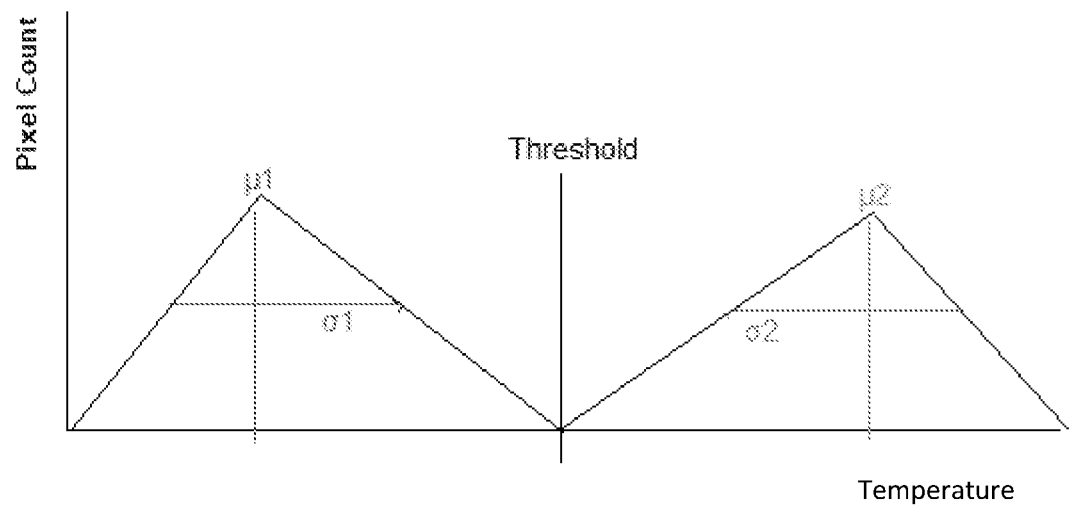
FIG. 5 illustrates a second possible statistical model used in the method of FIG. 2.

The computational burden of performing this process may be high. Optionally, it can be reduced by defining the statistical model on the assumption that, instead of the sum of two Gaussian distributions shown in FIG. 3, the distribution of the temperatures of the pixels is as shown in FIG. 5. Here the distribution contains a first triangular portion defined based on $\sigma_1$ and $\mu_1$, and a second triangular portion based on $\sigma_2$, and $\mu_2$. The two triangular portions may meet at a point which is used as the cut-off temperature.

Figure 7:
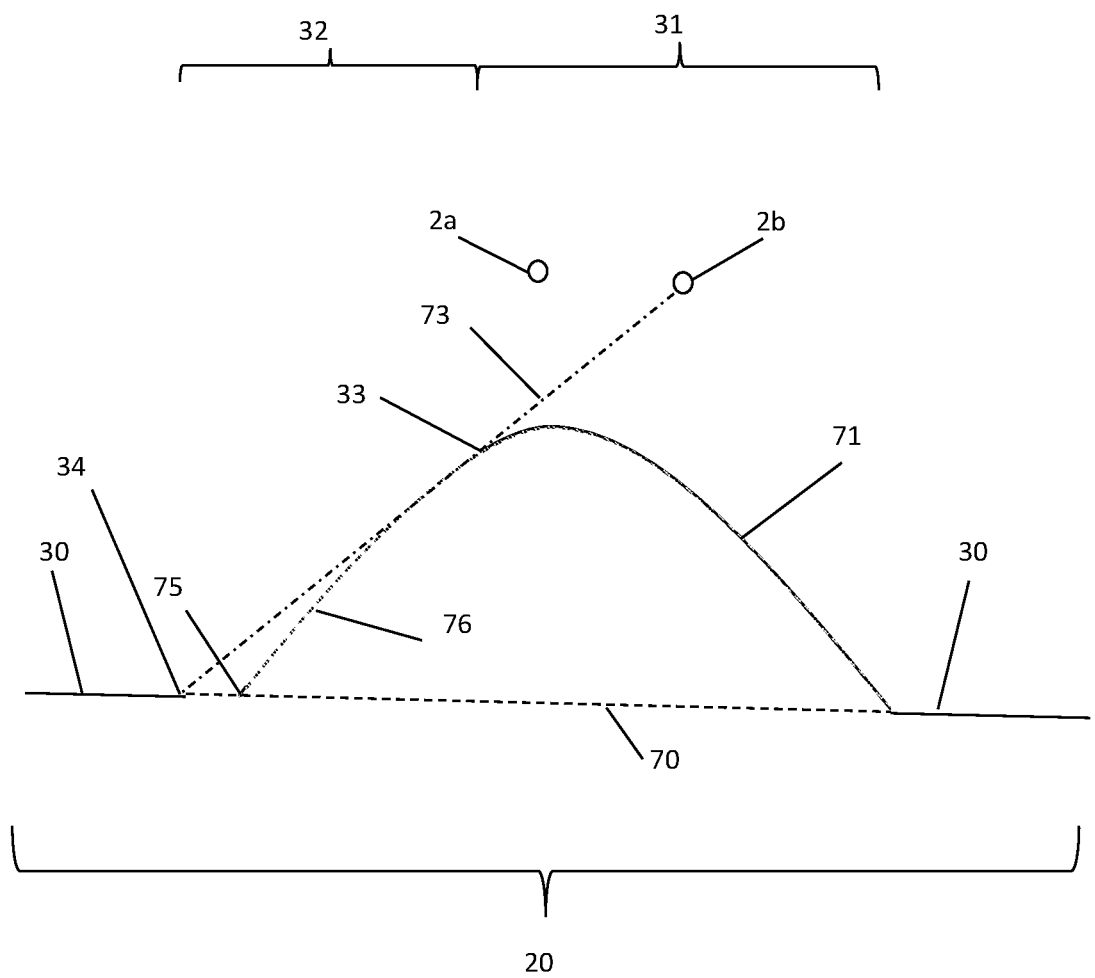
FIG. 7 illustrates an interpolation of the three-dimensional model of the skin profile performed in the method of FIG. 2.

In step 104 of method 100, the image data captured by the cameras 2a, 2b is used to produce a three-dimensional model of the region of the skin, e.g. by one of the conventional methods described above, such as stereoscopy. In step 105 any portions of the model which are defective, e.g. missing or not reliable (i.e. which meet a criterion indicative of not being reliable), may be identified. A portion of the model may be defective for one of several reasons. One, explained below with reference to FIG. 7, is that the corresponding portion of the skin was missing in at least one of the images captured by the cameras 2a, 2b due to occlusion. In this case, the defective portion of the model may be a gap in the model. Alternatively, the defective portion of the model may be present but may not be reliable, because it constructed based on inadequate data for it to be reliable. For example, each camera 2a, 2b may not be able to take reliable images of any portions of the skin range 20 which are farther from the camera 2a, 2b than a certain distance.

Figure 6A:
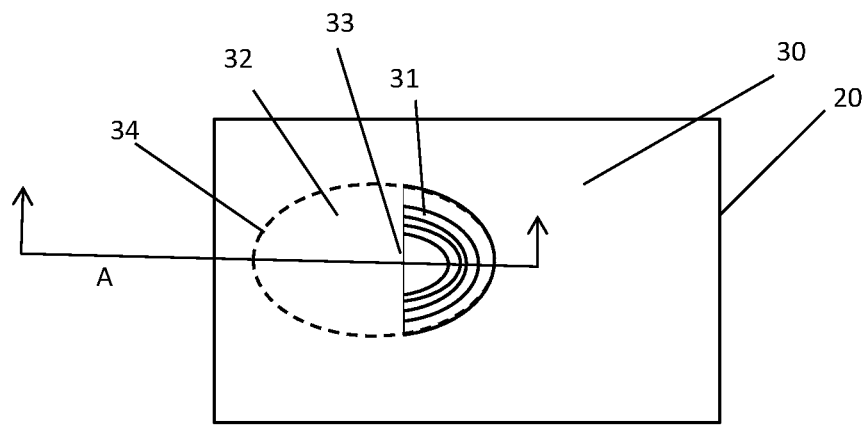
FIG. 6 is composed of FIG. 6(*a*) which is a three-dimensional model of the profile of the skin, and FIG. 6(*b*) which shows an enhanced segmentation produced by fusing an initial segmentation produced from temperature data, such as the segmentation of FIG. 4(*b*), with the three-dimensional model.

For example, the three dimensional model of the profile of the skin in region 20 (i.e. the skin for which the temperature dataset is available) is illustrated in FIG. 6(a) as a contour map. The three-dimensional model comprises a portion 30 which is not subject to the abnormality. This portion 30 may be identified from the three-dimensional model according to a continuity criterion. For example, the portion 30 may be substantially planar. In another example, the portion 30 may be (gently) curved but with a curvature which is both below a certain threshold and spatially uniform (to within a certain tolerance) throughout the portion 30. A baseline surface can be formed extending throughout the region 20. The baseline surface includes the portion 30 and additionally one or more portions which are formed by interpolation using the portion 30 (i.e. smoothly filling any gaps in the portion 30). The baseline surface is an estimate of how the skin profile would have been if the abnormality had not existed. The three-dimensional model further comprises a portion 31 which does not meet the continuity criterion, and which is thus likely to correspond approximately to the abnormality (tumor). In FIG. 6(a), the portion 31 is drawn including contours indicating lines on the three-dimensional model which differ from the baseline surface by equal amounts. A portion 32 of the three-dimensional model is identified as being defective (missing or unreliable). The defective portion 32 has a first edge 34 which meets the portion 30, and a second edge 33 which meets the portion 31.

Steps 104 and 105 may optionally be performed together as a single step.

Figure 6B:
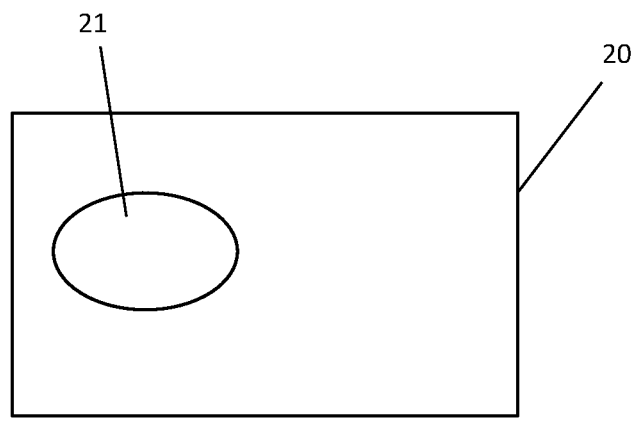

In step 106, the three-dimensional model is used to improve a segmentation obtained in step 103. Thus, the temperature dataset is "fused" with the model of the three-dimensional profile of the skin, to obtain an enhanced segmentation of the skin. For example, comparing FIGS. 4(b) and 6(a) which represent the same skin region, the region 22 of FIG. 4(b) corresponds to a part of FIG. 6(a) which is within the area 30. Thus, the region 22 can be reclassified as not being subject to the abnormality. This gives a final segmentation as shown in FIG. 6(b).

In step 107, the three-dimensional model of the profile of the skin region is modified (improved) in at least part of the defective portion of the three-dimensional model.

Before explaining step 107, we explain FIG. 7, which is a cross-sectional view of the three-dimensional skin model in the plane marked as A in FIG. 6(a). FIG. 7 shows also the positions of the cameras 2a, 2b. As mentioned above, the three-dimensional model was obtained by stereoscopy using images from the cameras 2a, 2b. FIG. 7 shows the portion 30 of the three-dimensional model meeting the continuity criterion. The baseline surface extends across the whole of the region 20. It comprises the portion 30 of the three-dimensional model which meets the continuity criterion and which includes a gap, corresponding to the portions 31 and 32 of the three-dimensional model. The baseline surface also comprises a portion 70 which is formed by smoothly interpolating the portion 30 across the gap. The portion 31 of the three-dimensional image corresponds to a portion 71 of the skin which overlies (i.e. is subject to) a tumor, and which is well-imaged because it is in the field of view of both cameras 2a, 2b.

From FIG. 7, it can be understood why a defective portion of the three-dimensional model exists. Although all the surface of skin protrusion is in the field of view of camera 2a, the defective portion 32 is not in the field of view of the camera 2b due to occlusion, so stereoscopy cannot be used to construct the portion 32 of the three-dimensional model. Specifically, the defective portion 32 extends between a line 33 where the line of sight 73 of the camera 2b intercepts the skin surface 71 (in FIG. 7, this line 33 appears as a point, where the line 33 intercepts the plane of the figure), and the line 34 where the line of sight 73 intercepts the baseline surface 30, 70 (again, in FIG. 7, the line 34 appears as a point, where the line 34 intercepts the plane of the figure). According to the segmentation model, there is a line in the defective portion 32 of the three-dimensional model which is the edge of the portion of the skin subject to the tumor. This line appears in FIG. 7 as the point 75, where the line intercepts the plane of the figure.

In step 107, the three-dimensional model is supplemented by adding to it an interpolation surface 76 which appears in FIG. 7 as a line, where the interpolation surface 76 intercepts the plane of the figure. The interpolation surface 76 has a first edge which is the edge 75 of the portion of the skin which is subject to the abnormality according to the segmentation obtained in step 106. This first edge 75 of the interpolation surface 76 lies on the baseline surface 30, 70. The interpolation surface 76 has a second edge which is the line 33. Thus, the added interpolation surface 76 is a good estimate of the surface of the skin within the defective portion 32 of the three-dimensional model.

The added interpolation surface 76 of the three-dimensional model is continuous with the surface 71 at the line 33. Furthermore, preferably the gradient (in three-dimensions) of the added surface 76 is equal to that of the surface 71 at the line 33. In other words, the gradient of the surface 71 at the line 33 (which can be obtained reliably, since surface 71 is reliable) is used to set the gradient of the interpolation surface 76 at the line 33.

In step 108, one or more numerical parameters characterizing the abnormality are derived (e.g. automatically) from the modified three-dimensional model of the profile of the skin, e.g. a value indicative of its volume. For example, the numerical parameter(s) may comprise a calculated volume between the portion of the modified three-dimensional model representing the skin over the tumor (i.e. the surfaces 71, 76), and the baseline surface 30, 70 of the skin, which represents the skin as it would have been in the absence of the abnormality.

Figure 8:
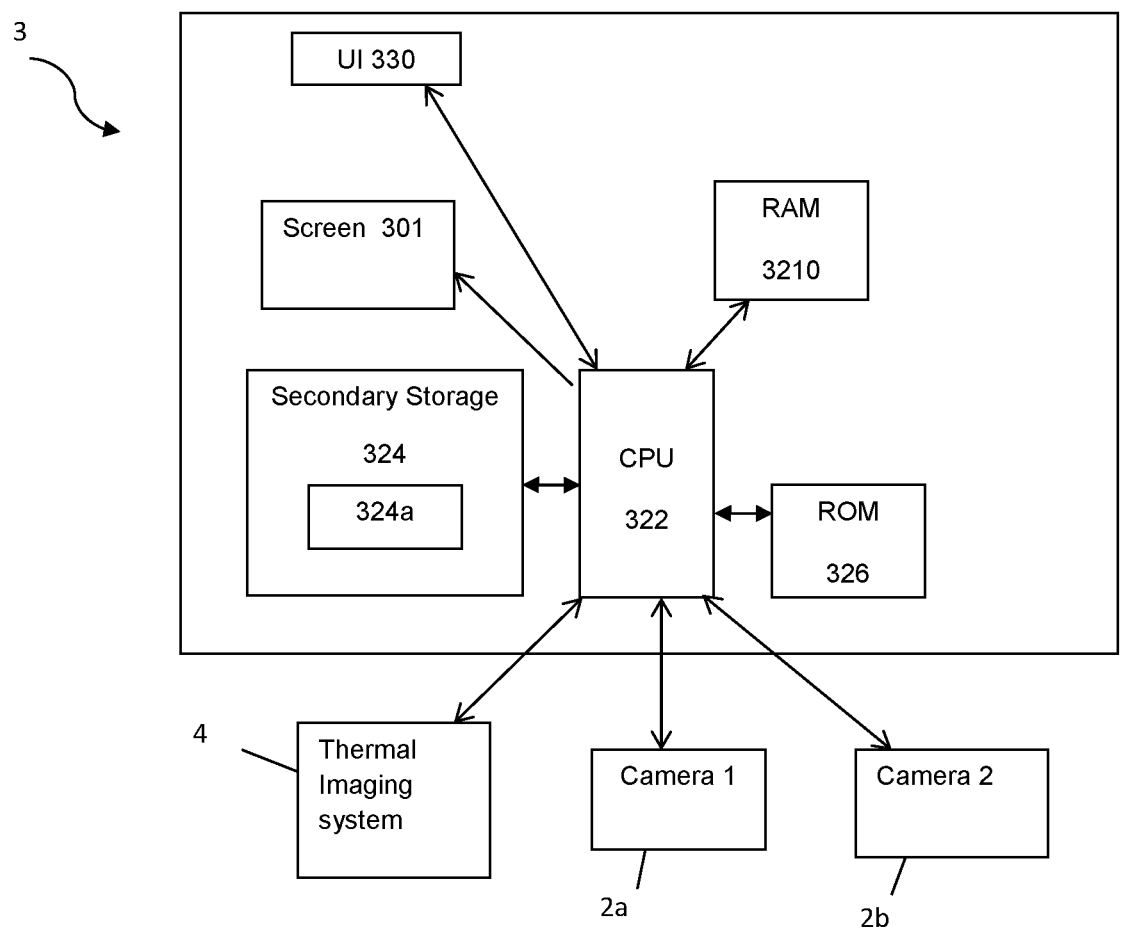
FIG. 8 illustrates the structure of a data processing system of the imaging system of FIG. 1.

FIG. 8 is a block diagram showing a technical architecture of the data processing system 3. The data processing system 3 includes a processor 322 (which may be referred to as a central processor unit or CPU) that is in communication with the image capture devices 2a, 2b, 4 for controlling when they capture images and for receiving the images.

The processor 322 is also in communication with memory devices including secondary storage 324 (such as disk drives or memory cards), read only memory (ROM) 326, and random access memory (RAM) 3210. The processor 322 may be implemented as one or more CPU chips.

The system 300 includes a user interface (UI) 330 for controlling the processor 322. The UI 330 may comprise a touch screen, keyboard, keypad or other known input device. If the UI 330 comprises a touch screen, the processor 322 is operative to generate an image on the touch screen. Alternatively, the system may include a separate screen 301 for displaying images under the control of the processor 322.

The secondary storage 324 typically comprises a memory card or other storage device and is used for non-volatile storage of data and as an over-flow data storage device if RAM 3210 is not large enough to hold all working data. Secondary storage 324 may be used to store programs which are loaded into RAM 3210 when such programs are selected for execution.

In this embodiment, the secondary storage 324 has an order generation component 324a, comprising non-transitory instructions operative by the processor 322 to perform various operations of the method of the present disclosure. The ROM 326 is used to store instructions and perhaps data which are read during program execution. The secondary storage 324, the RAM 3210, and/or the ROM 326 may be referred to in some contexts as computer readable storage media and/or non-transitory computer readable media.

The processor 322 executes instructions, codes, computer programs, scripts which it accesses from hard disk, floppy disk, optical disk (these various disk based systems may all be considered secondary storage 324), flash drive, ROM 326, or RAM 3210. While only one processor 322 is shown, multiple processors may be present. Thus, while instructions may be discussed as executed by a processor, the instructions may be executed simultaneously, serially, or otherwise executed by one or multiple processors.

Whilst the foregoing description has described exemplary embodiments, it will be understood by those skilled in the art that many variations of the embodiment can be made within the scope of the attached claims. For example, in the explanation of the embodiment given above, the skin of the animal exhibits a tumor, but the embodiment is equally applicable to a case in which the skin of the animal instead exhibits a wound. Also, certain steps of the method 100 may be performed in a different order and/or omitted. Furthermore, the method may optionally be performed by a distributed computer system including multiple processing units which mutually communicate over a communication network. The term "based on" is used in this document such that, if a process is said to be based on certain data, the process uses that data but may use other data also.

The invention claimed is:

1. A method of identifying at least one portion of the skin of an animal which is a region of interest, the method comprising:
   receiving a temperature dataset indicating the temperature of each of a plurality of points on the skin of the animal;
   using the temperature dataset to obtain an initial segmentation of the skin which classifies the skin into at least one portion of the skin which is part of the region of interest and at least one portion which is not part of the region of interest, and
   using a three dimensional model of the profile of the skin to enhance the initial segmentation by identifying at least one area of the initial segmentation which incorrectly classifies skin as part of the region of interest, and correcting the identified incorrect classification.

2. A method according to claim 1 in which the step of deriving an estimate of the portion of the region of the skin which is part of the region of interest, comprises using the temperature dataset to derive one or more cut-off temperatures, and generating a segmentation of the region of the skin, by determining whether, for each of a plurality of points in the region of the skin, the temperature of the point according to the temperature dataset is above or below one derived cut-off temperature.

3. A method according to claim 2 in which the one or more cut-off temperatures are derived from a statistical model of statistical variation of temperature within a region of the skin containing both skin which is part of the region of interest and skin which is not part of the region of interest, the cut-off temperature for a given point on the skin being a temperature at which the point of the skin is equally likely according to the statistical model to be subject or not part of the region of interest.

4. A method according to claim 3 in which the statistical model is characterized by a first temperature value indicative of an average temperature of skin points which are part of the region of interest, and a second temperature value indicative of an average temperature of skin points which are not part of the region of interest.

5. A method according to claim 4 in which the statistical model is further characterized by a first variance value indicative of a temperature variability of skin points which are part of the region of interest, and a second variance value indicative of a temperature variability of skin points which are not part of the region of interest.

6. A method according to claim 3 in which, according to the statistical model, the likelihood that any given point of the skin is part of the region of interest is further based on the temperatures, according to the temperature data, of one or more other points on the skin which each meet a proximity criterion with respect to the given point, whereby the derived cut-off temperature for the given point depends upon the temperatures of the corresponding other points.

7. A method according to claim 3, which comprises an iterative procedure in which, in each of a plurality of steps:
a current estimate of one of more numerical parameters of the statistical model is used to perform a candidate segmentation of the region of the skin, and
the candidate segmentation is used to produce an improved estimate of the one or more numerical parameters.

8. A method according to claim 1 further comprising capturing the temperature data.

9. A method of identifying at least one portion of the skin of an animal which is a region of interest, the method comprising:
receiving a temperature dataset indicating the temperature of each of a plurality of points on the skin of the animal;
identifying at least one defective portion of a three-dimensional model; and
modifying the three-dimensional model by adding to it an interpolation surface in at least part of the defective portion of the three-dimensional model, the interpolation surface having a first edge which, according to a segmentation based on the temperature data, is at an edge of a portion of the skin which is part of the region of interest.

10. A method according to claim 9 in which the interpolation surface has a second edge in a portion of the skin which is part of the region of interest according to the segmentation, the interpolation surface being continuous at the second edge with the three-dimensional model.

11. A method according to claim 10 in which, at the second edge, the interpolation surface has a gradient equal to the gradient of the three-dimensional model.

12. A method according to claim 9 further including deriving one or more numerical parameters characterizing a volume of an abnormality associated with the region of interest from the modified three-dimensional model of the profile of the skin.

13. A system comprising a processor and a data storage device storing program instructions operative, when implemented by the processor, to cause the processor to identify at least one portion of the skin of an animal which is a region of interest by:
receiving a temperature dataset indicating the temperature of each of a plurality of points on the skin of the animal;
using the temperature dataset to obtain an initial segmentation of the skin which classifies the skin into at least one portion of the skin which is part of the region of interest and at least one portion which is not part of the region of interest; and
using a three dimensional model of the profile of the skin to enhance the initial segmentation by identifying at least one area of the initial segmentation which incorrectly classifies skin as part of the region of interest, and correcting the identified incorrect classification.

14. A system according to claim 13 further comprising a thermal imaging system for generating the temperature dataset.

* * * * *